US006441153B1

(12) United States Patent
Donoho et al.

(10) Patent No.: US 6,441,153 B1
(45) Date of Patent: Aug. 27, 2002

(54) HUMAN CARBOXYPEPTIDASES AND POLYNUCLEOTIDES ENCODING THE SAME

(75) Inventors: Gregory Donoho; C. Alexander Turner, Jr., both of The Woodlands, TX (US); Michael C. Nehls, Stockdorf (DE); Glenn Friedrich, Houston, TX (US); Brian Zambrowicz, The Woodlands, TX (US); Arthur T. Sands, The Woodlands, TX (US)

(73) Assignee: Lexicon Genetics Incorporated, The Woodlands, TX (US)

( * ) Notice: Subject to any disclaimer, the term of this patent is extended or adjusted under 35 U.S.C. 154(b) by 0 days.

(21) Appl. No.: 09/675,305

(22) Filed: Sep. 29, 2000

Related U.S. Application Data

(60) Provisional application No. 60/156,685, filed on Sep. 29, 1999.

(51) Int. Cl.[7] .......................... C07H 21/04; C12N 9/64
(52) U.S. Cl. ...................... 536/23.2; 435/226
(58) Field of Search ......................... 536/23.2; 435/226

(56) References Cited

U.S. PATENT DOCUMENTS

| | | | |
|---|---|---|---|
| 4,215,051 A | 7/1980 | Schroeder et al. | 549/250 |
| 4,376,110 A | 3/1983 | David et al. | 435/5 |
| 4,946,778 A | 8/1990 | Ladner et al. | 435/69.6 |
| 5,474,901 A | 12/1995 | Drayna et al. | 485/7.4 |
| 5,593,674 A | 1/1997 | Drayna et al. | 424/94.65 |
| 5,837,458 A | 11/1998 | Minshull et al. | 435/6 |
| 5,869,336 A | 2/1999 | Meyer et al. | 435/348 |
| 5,877,397 A | 3/1999 | Lonberg et al. | 800/18 |
| 6,075,181 A | 6/2000 | Kucherlapati et al. | 800/25 |

FOREIGN PATENT DOCUMENTS

| | | |
|---|---|---|
| WO | WO 96 23064 A | 8/1996 |
| WO | WO 98 35988 A | 8/1998 |

OTHER PUBLICATIONS

Bird et al, 1988, "Single–Chain Antigen–Binding Proteins", Science 242:423–426.
Bitter et al, 1987, "Expression and Secretion Vectors for Yeast", Methods in Enzymology 153:516–544.
Colbere–Garapin et al, 1981, "A New Dominant Hybrid Selective Marker for Higher Eukaryotic Cells", J. Mol. Biol. 150:1–14.
Gautier et al, 1987, "α–DNA IV:αanomeric and β–anomeric tetrathymidylates covalently linked to intercalating oxazolopyridocarbazole. Synthesis, physiochemical properties and poly (rA) binding", Nucleic Acids Research 15(16):6625–6641.
Greenspan et al, 1993, "Idiotypes: structure and immunogenicity", FASEB Journal 7:437–444.
Huse et al, 1989, "Generation of a Large Combinatorial Library of the Immunoglobulin Repertoire in Phage Lambda", Science 246:1275–1281.
Huston et al, 1988, "Protein engineering of antibody binding sites: Recovery of specific activity in an anti–digoxin single–chain Fv analogue produced in *Escherichia coli*", Proc. Natl. Acad. Sci. USA 85:5879–5883.
Inoue et al, 1987, "Sequence–dependent hydrolysis of RNA using modified oligonucleotide splints and R Nase H", FEBS Letters 215(2):327–330.
Inoue et al, 1987, "Synthesis and hybridization studies on two complementary nona(2'–O–methyl)ribonucleotides", Nucleic Acids Research 15(15):6131–6149.
Inouye & Inouye, 1985, "Up–promoter mutations in the Ipp gene of *Escherichia coli*", Nucleic Acids Research 13(9):3101–3110.
Janknecht et al, 1991, "Rapid and efficient purification of native histidine–tagged protein expressed by recombinant vaccinia virus", PNAS USA 88:8972–8976.
Kohler & Milstein, 1975, "Continuous cultures of fused cells secreting antibody of predefined specificity", Nature 256:495–497.
Logan et al, 1984, "Adenovirus tripartite leader sequence enhances translation of mRNAs late after infection", Proc. Natl. Acad. Sci. USA 81:3655–3659.
Lowy et al, 1980, "Isolation of Transforming DNA: Cloning the Hamster aprt Gene", Cell 22:817–823.
Morrison et al, 1984, "Chimeric human antibody molecules: Mouse antigen–binding domains with human constant region domains", Proc. Natl. Acad. Sci. USA 81:6851–6855.
Mulligan & Berg, 1981, "Selection for animal cells that express the *Escherichia coli* gene coding for xanthine–guanine phosphoribosyltransferase", Proc. Natl. Acad. Sci. USA 78(4):2072–2076.
Neuberger et al, 1984, "Recombinant antibodies possessing novel effector functions", Nature 312:604–608.
Nisonoff, 1991, "Idiotypes: Concepts and Applications", J. of Immunology 147:2429–2438.
O'Hare et al, 1981, "Transformation of mouse fibroblasts to methotrexate resistance by a recombinant plasmid expressing a prokaryotic dihydrofolate reductase", Proc. Natl. Acad. Sci. USA 78(3):1527–1531.
Ruther et al, 1983, "Easy identification of cDNA clones", EMBO Journal 2(10):1791–1794.
Santerre et al, 1984, "Expression of prokaryotic genes for hygromycin B and G418 resistance as dominant–selection markers in mouse L cells", Gene 30:147–156.
Sarin et al., 1988, "Inhibition of acquired immunodeficiency syndrome virus by oligodeoxynucleoside methylphosphonates", Proc. Natl. Acad. Sci. USA 85:7448–7451.

(List continued on next page.)

*Primary Examiner*—Elizabeth Slobodyansky

(57) ABSTRACT

Novel human polynucleotide and polypeptide sequences are disclosed that can be used in therapeutic, diagnostic, and pharmacogenomic applications.

2 Claims, No Drawings

OTHER PUBLICATIONS

Smith et al, 1983, "Molecular Engineering of the Autographa californica Nuclear Polyhedrosis Virus Genome: Deletion of Mutations within the Polyhedrin Gene", J. Virol. 46(2):584–593.

Stein et al, 1988, "Physiochemical properties of phosphorothioate oligodeoxynucleotides", Nucleic Acids Research 16(8):3209–3221.

Szybalska & Szybalski, 1962, "Genetics of Human Cell Lines, IV. DNA–Mediated Heritable Transformation of a Biochemical Trait", Proc. Natl. Acad. Sci. USA 48:2026–2034.

Takeda et al, 1985, "Construction of chimaeric processed immunoglobulin genes containing mouse variable and human constant regions sequences", Nature 314:452–454.

Van Heeke et al, 1989, "Expression of Human Asparagine Synthetase in *Escherichia coli*", J. Biol. Chemistry 264(10):5503–5509.

Ward et al, 1989, "Binding activities of a repertoire of single immunoglobulin variable domains secreted from *Escherichia coli*", Nature 341:544–546.

Wigler et al, 1980, "Transformation of mammalian cells with an amplifiable dominant–acting gene", Proc. Natl. Acad. Sci. USA 77(6):3567–3570.

Wigler et al, 1977, "Transfer of Purified Herpes Virus Thymidine Kinase Gene to Cultured Mouse Cells", Cell 11:223–232.

EMBL Database, Heidelberg, FRG, Emest accession No. H86718, Nov. 22, 1995 Hillier, L. et al.: "yt08c10r1 Soares retina N2b5HR Homo Sapiens cDNA clone IMAGE: 223698 5', mRNA sequence" XP002162175.

EMBL Database, Heidelberg, FRG Emhum2 accession No. AF221594, Aug. 2, 2000 Gu, J. et al.: "Homo sapiens carboxypeptidase B precursor (CPAH) mRNA, complete cds." XP002162176.

HUMAN CARBOXYPEPTIDASES AND POLYNUCLEOTIDES ENCODING THE SAME

The present application claims the benefit of U.S. Provisional Application No. 60/156,685 which was filed on Sep. 29, 1999 and is herein incorporated by reference in its entirety.

INTRODUCTION

The present invention relates to the discovery, identification, and characterization of novel human polynucleotides encoding proteins that share sequence similarity with animal proteases. The invention encompasses the described polynucleotides, host cell expression systems, the encoded proteins, fusion proteins, polypeptides and peptides, antibodies to the encoded proteins and peptides, and genetically engineered animals that either lack or over express the disclosed genes, antagonists and agonists of the proteins, and other compounds that modulate the expression or activity of the proteins encoded by the disclosed sequences that can be used for diagnosis, drug screening, clinical trial monitoring and the treatment of physiological disorders.

BACKGROUND OF THE INVENTION

Proteases are enzymes that cleave polypeptide sequences. Carboxypeptidases are proteases that hydrolyze the peptide bonds at the carboxy-terminal end of a chain of amino acids and have been identified in a wide variety of cell types and animals. Peptidases have been implicated in a wide variety of biological processes including, but not limited to, digestion, coagulation, diabetes, prostate cancer, gynecological disorders, neurological disorders, and obesity. Accordingly, peptidases represent significant targets for regulatory control of a variety of physiological processes and pathways.

SUMMARY OF THE INVENTION

The present invention relates to the discovery, identification, and characterization of nucleotides that encode novel human proteins, and the corresponding amino acid sequences of these proteins. The novel human proteins (NHPs) described for the first time herein share structural similarity with animal proteases, and especially carboxypeptidases. As such, the described NHPs represent a new family of protease-related proteins with a range of homologues and orthologs that transcend phyla and a broad range of species.

The novel human nucleic acid sequences described herein, encode proteins/open reading frames (ORFS) of 47, 88, 247, 92, 437, and 350 amino acids in length (see SEQ ID NOS: 2, 4, 6, 8, 10 and 12 respectively).

The invention also encompasses agonists and antagonists of the described NHPs, including small molecules, large molecules, mutant NHPs, or portions thereof that compete with native NHP, peptides, and antibodies, as well as nucleotide sequences that can be used to inhibit the expression of the described NHPs (e.g., antisense and ribozyme molecules, and gene or regulatory sequence replacement constructs) or to enhance the expression of the described NHP sequences (e.g., expression constructs that place the described sequence under the control of a strong promoter system), and transgenic animals that express a NHP transgene, or "knock-outs" (which can be conditional) that do not express a functional NHP.

Further, the present invention also relates to processes of identifying compounds that modulate, i.e., act as agonists or antagonists, of NHP expression and/or NHP product activity that utilize purified preparations of the described NHPs and/or NHP product, or cells expressing the same. Such compounds can be used as therapeutic agents for the treatment of any of a wide variety of symptoms associated with biological disorders or imbalances.

DESCRIPTION OF THE SEQUENCE LISTING AND FIGURES

The Sequence Listing provides the sequences of 6 protease-related ORFs that encode the described NHP amino acid sequences.

DETAILED DESCRIPTION OF THE INVENTION

The NHPs, described for the first time herein, are novel proteins that are expressed in, inter alia, human cell lines, and human brain, pituitary, spinal cord, thymus, spleen, lymph node, bone marrow, trachea, lung, kidney, prostate, testis, thyroid, adrenal gland, stomach, small intestine colon, skeletal muscle, uterus, mammary gland, bladder, and cervix cells. The described sequences were compiled from gene trapped cDNAs and a clone isolated from a human prostate cDNA library (Edge Biosystems, Gaithersburg, Md.). The present invention encompasses the nucleotides presented in the Sequence Listing, host cells expressing such nucleotides, the expression products of such nucleotides, and: (a) nucleotides that encode mammalian homologs of the described genes, including the specifically described NHPs, and the NHP products; (b) nucleotides that encode one or more portions of the NHPs that correspond to functional domains, and the polypeptide products specified by such nucleotide sequences, including but not limited to the novel regions of any active domain(s); (c) isolated nucleotides that encode mutant versions, engineered or naturally occurring, of the described NHPs in which all or a part of at least one domain is deleted or altered, and the polypeptide products specified by such nucleotide sequences, including but not limited to soluble proteins and peptides in which all or a portion of the signal sequence in deleted; (d) nucleotides that encode chimeric fusion proteins containing all or a portion of a coding region of an NHP, or one of its domains (e.g., a receptor/ligand binding domain, accessory protein/self-association domain, etc.) fused to another peptide or polypeptide; or (e) therapeutic or diagnostic derivatives of the described polynucleotides such as oligonucleotides, antisense polynucleotides, ribozymes, dsRNA, or gene therapy constructs comprising a sequence first disclosed in the Sequence Listing.

As discussed above, the present invention includes: (a) the human DNA sequences presented in the Sequence Listing (and vectors comprising the same) and additionally contemplates any nucleotide sequence encoding a contiguous NHP open reading frame (ORF) that hybridizes to a complement of a DNA sequence presented in the Sequence Listing under highly stringent conditions, e.g., hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3) and encodes a functionally equivalent gene product. Additionally contemplated are any nucleotide sequences that hybridize to the complement of the DNA sequence that encode and express an amino acid sequence presented in the Sequence Listing under moderately stringent conditions, e.g., washing in 0.2×SSC/0.1% SDS at 42° C. (Ausubel et al., 1989, supra), yet still encode a functionally equivalent NHP product. Functional equivalents of a NHP include naturally occurring NHPs present in other species and mutant NHPs whether naturally occurring or engineered (by site directed mutagenesis, gene shuffling, directed evolution as described in, for example, U.S. Pat. No. 5,837,458). The invention also includes degenerate nucleic acid variants of the disclosed NHP polynucleotide sequences.

Additionally contemplated are polynucleotides encoding NHP ORFs, or their functional equivalents, encoded by polynucleotide sequences that are about 99, 95, 90, or about 85 percent similar to corresponding regions of SEQ ID NO:1 (as measured by BLAST sequence comparison analysis using, for example, the GCG sequence analysis package using default parameters).

The invention also includes nucleic acid molecules, preferably DNA molecules, that hybridize to, and are therefore the complements of, the described NHP gene nucleotide sequences. Such hybridization conditions may be highly stringent or less highly stringent, as described above. In instances where the nucleic acid molecules are deoxyoligonucleotides ("DNA oligos"), such molecules are generally about 16 to about 100 bases long, or about 20 to about 80, or about 34 to about 45 bases long, or any variation or combination of sizes represented therein that incorporate a contiguous region of sequence first disclosed in the Sequence Listing. Such oligonucleotides can be used in conjunction with the polymerase chain reaction (PCR) to screen libraries, isolate clones, and prepare cloning and sequencing templates, etc.

Alternatively, such NHP oligonucleotides can be used as hybridization probes for screening libraries, and assessing gene expression patterns (particularly using a micro array or high-throughput "chip" format). Additionally, a series of the described NHP oligonucleotide sequences, or the complements thereof, can be used to represent all or a portion of the described NHP sequences. The oligonucleotides, typically between about 16 to about 40 (or any whole number within the stated range) nucleotides in length may partially overlap each other and/or the NHP sequence may be represented using oligonucleotides that do not overlap. Accordingly, the described NHP polynucleotide sequences shall typically comprise at least about two or three distinct oligonucleotide sequences of at least about 18, and preferably about 25, nucleotides in length that are each first disclosed in the described Sequence Listing. Such oligonucleotide sequences may begin at any nucleotide present within a sequence in the Sequence Listing and proceed in either a sense (5'-to-3') orientation vis-a-vis the described sequence or in an antisense orientation.

For oligonucleotide probes, highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as NHP sequence antisense molecules, useful, for example, in NHP sequence regulation (for and/or as antisense primers in amplification reactions of NHP nucleic acid sequences). With respect to NHP sequence regulation, such techniques can be used to regulate biological functions. Further, such sequences may be used as part of ribozyme and/or triple helix sequences that are also useful for NHP sequence regulation.

Inhibitory antisense or double stranded oligonucleotides can additionally comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide can also comprise at least one modified sugar moiety selected from the group including but not limited to arabinose, 2-fluoroarabinose, xylulose, and hexose.

In yet another embodiment, the antisense oligonucleotide will comprise at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330). Alternatively, double stranded RNA can be used to disrupt the expression and function of a targeted NHP.

Oligonucleotides of the invention can be synthesized by standard methods known in the art, e.g. by use of an automated DNA synthesizer (such as are commercially available from Biosearch, Applied Biosystems, etc.). As examples, phosphorothioate oligonucleotides can be synthesized by the method of Stein et al. (1988, Nucl. Acids Res. 16:3209), and methylphosphonate oligonucleotides can be prepared by use of controlled pore glass polymer supports (Sarin et al., 1988, Proc. Natl. Acad. Sci. U.S.A. 85:7448–7451), etc.

Low stringency conditions are well known to those of skill in the art, and will vary predictably depending on the specific organisms from which the library and the labeled sequences are derived. For guidance regarding such conditions see, for example, Sambrook et al., 1989, Molecular Cloning, A Laboratory Manual (and periodic updates thereof), Cold Springs Harbor Press, N.Y.; and Ausubel et al., 1989, Current Protocols in Molecular Biology, Green Publishing Associates and Wiley Interscience, N.Y.

Alternatively, suitably labeled NHP nucleotide probes can be used to screen a human genomic library using appropriately stringent conditions or by PCR. The identification and characterization of human genomic clones is helpful for identifying polymorphisms (including, but not limited to, nucleotide repeats, microsatellite alleles, single nucleotide polymorphisms, or coding single nucleotide polymorphisms), determining the genomic structure of a given locus/allele, and designing diagnostic tests. For example, sequences derived from regions adjacent to the intron/exon boundaries of the human gene can be used to design primers for use in amplification assays to detect mutations within the exons, introns, splice sites (e.g., splice acceptor and/or donor sites), etc., that can be used in diagnostics and pharmacogenomics.

Further, a NHP sequence homolog can be isolated from nucleic acid from an organism of interest by performing PCR using two degenerate or "wobble" oligonucleotide primer pools designed on the basis of amino acid sequences within the NHP products disclosed herein. The template for the reaction may be total RNA, mRNA, and/or cDNA obtained by reverse transcription of mRNA prepared from, for example, human or non-human cell lines or tissue known or suspected to express an allele of a NHP sequence.

The PCR product can be subcloned and sequenced to ensure that the amplified sequences represent the sequence of the desired NHP gene. The PCR fragment can then be used to isolate a full length cDNA clone by a variety of methods. For example, the amplified fragment can be labeled and used to screen a cDNA library, such as a bacteriophage cDNA library. Alternatively, the labeled fragment can be used to isolate genomic clones via the screening of a genomic library.

PCR technology can also be used to isolate full length CDNA sequences. For example, RNA can be isolated, following standard procedures, from an appropriate cellular or tissue source (i.e., one known, or suspected, to express a NHP sequence, such as, for example, testis tissue). A reverse transcription (RT) reaction can be performed on the RNA using an oligonucleotide primer specific for the most 5' end of the amplified fragment for the priming of first strand synthesis. The resulting RNA/DNA hybrid may then be "tailed" using a standard terminal transferase reaction, the hybrid may be digested with RNase H, and second strand synthesis may then be primed with a complementary primer. Thus, cDNA sequences upstream of the amplified fragment can be isolated. For a review of cloning strategies that can be used, see e.g., Sambrook et al., 1989, supra.

A cDNA encoding a mutant NHP sequence can be isolated, for example, by using PCR. In this case, the first cDNA strand can be synthesized by hybridizing an oligo-dT oligonucleotide to mRNA isolated from tissue known or suspected to be expressed in an individual putatively carrying a mutant NHP allele, and by extending the new strand with reverse transcriptase. The second strand of the cDNA is then synthesized using an oligonucleotide that hybridizes specifically to the 5' end of the normal gene. Using these two primers, the product is then amplified via PCR, optionally cloned into a suitable vector, and subjected to DNA sequence analysis through methods well known to those of skill in the art. By comparing the DNA sequence of the mutant NHP allele to that of a corresponding normal NHP allele, the mutation(s) responsible for the loss or alteration of function of the mutant NHP sequence product can be ascertained.

Alternatively, a genomic library can be constructed using DNA obtained from an individual suspected of or known to carry a mutant NHP allele (e.g., a person manifesting a NHP-associated phenotype such as, for example, obesity, high blood pressure, etc.), or a CDNA library can be constructed using RNA from a tissue known, or suspected, to express a mutant NHP allele. A normal NHP sequence, or any suitable fragment thereof, can then be labeled and used as a probe to identify the corresponding mutant NHP allele in such libraries. Clones containing mutant NHP coding sequences can then be purified and subjected to sequence analysis according to methods well known to those skilled in the art.

Additionally, an expression library can be constructed utilizing cDNA synthesized from, for example, RNA isolated from a tissue known, or suspected, to express a mutant NHP allele in an individual suspected of or known to carry such a mutant allele. In this manner, gene products made by the putatively mutant tissue may be expressed and screened using standard antibody screening techniques in conjunction with antibodies raised against a normal NHP product, as described below. (For screening techniques, see, for example, Harlow, E. and Lane, eds., 1988, "Antibodies: A Laboratory Manual", Cold Spring Harbor Press, Cold Spring Harbor.)

Additionally, screening can be accomplished using labeled NHP fusion proteins, such as, for example, alkaline phosphatase-NHP or NHP-alkaline phosphatase fusion proteins. In cases where a NHP mutation results in an expressed gene product with altered function (e.g., as a result of a missense or a frameshift mutation), polyclonal antibodies to a NHP are likely to cross-react with a corresponding mutant NHP sequence product. Library clones detected via their reaction with such labeled antibodies can be purified and subjected to sequence analysis according to methods well known in the art.

The invention also encompasses (a) DNA vectors that contain any of the foregoing NHP coding sequences and/or their complements (i.e., antisense); (b) DNA expression vectors that contain any of the foregoing NHP coding sequences operatively associated with a regulatory element that directs the expression of the coding sequences (for example, baculo virus as described in U.S. Pat. No. 5,869,336 herein incorporated by reference); (c) genetically engineered host cells that contain any of the foregoing NHP coding sequences operatively associated with a regulatory element that directs the expression of the coding sequences in the host cell; and (d) genetically engineered host cells that express an endogenous NHP sequence under the control of an exogenously introduced regulatory element (i.e., gene activation). As used herein, regulatory elements include, but are not limited to, inducible and non-inducible promoters, enhancers, operators and other elements known to those skilled in the art that drive and regulate expression. Such regulatory elements include but are not limited to the human cytomegalovirus (hCMV) immediate early gene, regulatable, viral elements (particularly retroviral LTR promoters), the early or late promoters of SV40 adenovirus, the lac system, the trp system, the TAC system, the TRC system, the major operator and promoter regions of phage lambda, the control regions of fd coat protein, the promoter for 3-phosphoglycerate kinase (PGK), the promoters of acid phosphatase, and the promoters of the yeast α-mating factors.

The present invention also encompasses antibodies and anti-idiotypic antibodies (including Fab fragments), antagonists and agonists of the NHP, as well as compounds or nucleotide constructs that inhibit expression of a NHP sequence (transcription factor inhibitors, antisense and ribozyme molecules, or gene or regulatory sequence replacement constructs), or promote the expression of a NHP (e.g., expression constructs in which NHP coding sequences are operatively associated with expression control elements such as promoters, promoter/enhancers, etc.).

The NHPs or NHP peptides, NHP fusion proteins, NHP nucleotide sequences, antibodies, antagonists and agonists can be useful for the detection of mutant NHPs or inappropriately expressed NHPs for the diagnosis of disease. The NHP proteins or peptides, NHP fusion proteins, NHP nucleotide sequences, host cell expression systems, antibodies, antagonists, agonists and genetically engineered cells and animals can be used for screening for drugs (or high throughput screening of combinatorial libraries) effective in the treatment of the symptomatic or phenotypic manifestations of perturbing the normal function of NHP in the body. The use of engineered host cells and/or animals may offer an advantage in that such systems allow not only for the identification of compounds that bind to an endogenous receptor/ligand of a NHP, but can also identify compounds that trigger NHP-mediated activity.

Finally, the NHP products can be used as therapeutics. For example, soluble versions or derivatives of a NHP, or peptides/domains corresponding a NHP, NHP fusion protein products (especially NHP-Ig fusion proteins, i.e., fusions of a NHP, or a domain of a NHP, to an IgFc), NHP antibodies and anti-idiotypic antibodies (including Fab fragments), antagonists or agonists (including compounds that modulate or act on downstream targets in a NHP-mediated pathway) can be used to directly treat diseases or disorders. For instance, the administration of an effective amount of soluble NHP, or a NHP-IgFc fusion protein or an anti-idiotypic antibody (or its Fab) that mimics the NHP could activate or effectively antagonize NHP function. Nucleotide constructs encoding such NHP products can be used to genetically engineer host cells to express such products in vivo; these genetically engineered cells function as "bioreactors" in the body delivering a continuous supply of a NHP, a NHP peptide, or a NHP fusion protein to the body. Nucleotide constructs encoding functional NHPS, mutant NHPs, as well as antisense and ribozyme molecules can also be used in "gene therapy" approaches for the modulation of NHP expression. Thus, the invention also encompasses pharmaceutical formulations and methods for treating biological disorders.

Various aspects of the invention are described in greater detail in the subsections below.

The NHP Sequences

The cDNA sequences and the corresponding deduced amino acid sequences of the described NHPs are presented in the Sequence Listing. The NHP sequences were obtained from a human prostate cDNA library using probes and/or primers generated from human gene trapped sequence tags. Expression analysis has provided evidence that the described NHPs can be expressed, for example, in a variety of human cell types and that the described NHPs share significant similarity to a variety of proteases, and especially carboxypeptidase B or carboxypeptidase A, from, inter alia, humans, mice, and rats. SEQ ID NO: 13 describes a full length NHP ORF with flanking 5' and 3' sequences.

NHPs and NHP Polypeptides

NHPS, polypeptides, peptide fragments, mutated, truncated, or deleted forms of the NHPs, and/or NHP fusion proteins can be prepared for a variety of uses. These uses include, but are not limited to, the generation of antibodies, as reagents in diagnostic assays, for the identification of other cellular gene products related to a NHP, as reagents in assays for screening for compounds that can be as pharmaceutical reagents useful in the therapeutic treatment of mental, biological, or medical disorders and disease. Several uses and applications for plasma carboxypeptidases similar to those described herein are described in U.S. Pat. No. 5,593,674, the disclosure of which is herein incorporated by reference in its entirety.

The Sequence Listing discloses the amino acid sequences encoded by the described NHP polynucleotides. The NHPs have initiator methionines in DNA sequence contexts consistent with a translation initiation site and a hydrophobic signal-like sequence is present near the N-terminal region of the protein. The sequence data presented herein indicate that alternatively spliced forms of the NHPs exist (which may or may not be tissue specific).

The NHP amino acid sequences of the invention include the nucleotide and amino acid sequences presented in the Sequence Listing as well as analogues and derivatives thereof. Further, corresponding NHP homologues from other species are encompassed by the invention. In fact, any NHP protein encoded by the NHP nucleotide sequences described above, are within the scope of the invention, as are any novel polynucleotide sequences encoding all or any novel portion of an amino acid sequence presented in the Sequence Listing. The degenerate nature of the genetic code is well known, and, accordingly, each amino acid presented in the Sequence Listing, is generically representative of the well known nucleic acid "triplet" codon, or in many cases codons, that can encode the amino acid. As such, as contemplated herein, the amino acid sequences presented in the Sequence Listing, when taken together with the genetic code (see, for example, Table 4-1 at page 109 of "Molecular Cell Biology", 1986, J. Darnell et al. eds., Scientific American Books, New York, N.Y., herein incorporated by reference) are generically representative of all the various permutations and combinations of nucleic acid sequences that can encode such amino acid sequences.

The invention also encompasses proteins that are functionally equivalent to the NHPs encoded by the presently described nucleotide sequences as judged by any of a number of criteria, including, but not limited to, the ability to bind and cleave a substrate of a NHP, or the ability to effect an identical or complementary downstream pathway, or a change in cellular metabolism (e.g., proteolytic activity, ion flux, tyrosine phosphorylation, etc.). Such functionally equivalent NHP proteins include, but are not limited to, additions or substitutions of amino acid residues within the amino acid sequence encoded by the NHP nucleotide sequences described above, but which result in a silent change, thus producing a functionally equivalent gene product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

A variety of host-expression vector systems can be used to express the NHP nucleotide sequences of the invention. The presently described NHPS are similar to plasma carboxypeptidase B and are likely soluble proteins. Where the NHP peptide or polypeptide to be expressed is a soluble NHP protein, or a NHP peptide derived from a substantially nonhydrophobic domain of a NHP, or a truncated or deleted NHP the peptide or polypeptide can be recovered from the culture, i.e., from the host cell in cases where the NHP peptide or polypeptide is not secreted, or from the culture media in cases where the NHP peptide or polypeptide is secreted by the cells. However, such expression systems also encompass engineered host cells that express a NHP, or functional equivalent, in situ, i.e., anchored in the cell membrane. Purification or enrichment of a NHP from such expression systems can be accomplished using appropriate detergents and lipid micelles and methods well known to those skilled in the art. However, such engineered host cells themselves may be used in situations where it is important not only to retain the structural and functional characteristics of the NHP, but to assess biological activity, e.g., in drug screening assays.

The expression systems that can be used for purposes of the invention include but are not limited to microorganisms such as bacteria (e.g., E. coli, B. subtilis) transformed with recombinant bacteriophage DNA, plasmid DNA or cosmid DNA expression vectors containing NHP nucleotide sequences; yeast (e.g., Saccharomyces, Pichia) transformed with recombinant yeast expression vectors containing NHP nucleotide sequences; insect cell systems infected with recombinant virus expression vectors (e.g., baculovirus) containing NHP sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing NHP nucleotide sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors can be advantageously selected depending upon the use intended for the NHP product being expressed. For example, when a large quantity of such a protein is to be produced for the generation of pharmaceutical compositions of or containing NHP, or for raising antibodies to a NHP, vectors that direct the expression of high levels of fusion protein products that are readily purified may be desirable. Such vectors include, but are not limited to, the E. coli expression vector pUR278 (Ruther et al., 1983, EMBO J. 2:1791), in which a NHP coding sequence may be ligated individually into the vector in frame with the lacZ coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned target sequence product can be released from the GST moiety.

In an insect system, Autographa californica nuclear polyhidrosis virus (AcNPV) is used as a vector to express foreign sequences. The virus grows in Spodoptera frugiperda cells. A NHP coding sequence may be cloned individually into non-essential regions (for example the polyhedrin gene) of the virus and placed under control of an AcNPV promoter (for example the polyhedrin promoter). Successful insertion of NHP coding sequence will result in inactivation of the polyhedrin gene and production of non-occluded recombinant virus (i.e., virus lacking the proteinaceous coat coded for by the polyhedrin gene). These recombinant viruses are then used to infect Spodoptera frugiperda cells in which the inserted sequence is expressed (e.g., see Smith et al., 1983, J. Virol. 46: 584; Smith, U.S. Pat. No. 4,215,051).

In mammalian host cells, a number of viral-based expression systems may be utilized. In cases where an adenovirus is used as an expression vector, the NHP nucleotide sequence of interest may be ligated to an adenovirus transcription/translation control complex, e.g., the late promoter and tripartite leader sequence. This chimeric sequence may then be inserted in the adenovirus genome by in vitro or in vivo recombination. Insertion in a non-essential region of the viral genome (e.g., region E1 or E3) will result in a recombinant virus that is viable and capable of expressing a NHP product in infected hosts (e.g., See Logan & Shenk, 1984, Proc. Natl. Acad. Sci. USA 81:3655–3659). Specific initiation signals may also be required for efficient translation of inserted NHP nucleotide sequences. These signals include the ATG initiation codon and adjacent sequences. In cases where an entire NHP sequence or cDNA, including its own initiation codon and adjacent sequences, is inserted into the appropriate expression vector, no additional translational control signals may be needed. However, in cases where only a portion of a NHP coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (See Bittner et al., 1987, Methods in Enzymol. 153:516–544).

In addition, a host cell strain may be chosen that modulates the expression of the inserted sequences, or modifies and processes the sequence product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, VERO, BHK, HeLa, COS, MDCK, 293, 3T3, WI38, and in particular, human cell lines.

For long-term, high-yield production of recombinant proteins, stable expression is preferred. For example, cell lines which stably express the NHP sequences described above may be engineered. Rather than using expression vectors which contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the NHP product. Such engineered cell lines may be particularly useful in screening and evaluation of compounds that affect the endogenous activity of the NHP product.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk$^-$, hgprt$^-$ or aprt$^-$ cells, respectively. Also, antimetabolite resistance can be used as the basis of selection for the following genes: dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147).

Alternatively, any fusion protein may be readily purified by utilizing an antibody specific for the fusion protein being expressed. For example, a system described by Janknecht et al. allows for the ready purification of non-denatured fusion proteins expressed in human cell lines (Janknecht, et al., 1991, Proc. Natl. Acad. Sci. USA 88: 8972–8976). In this system, the sequence of interest is subcloned into a vaccinia recombination plasmid such that the sequence's open reading frame is translationally fused to an amino-terminal tag consisting of six histidine residues. Extracts from cells infected with recombinant vaccinia virus are loaded onto $Ni^{2+}$.nitriloacetic acid-agarose columns and histidine-tagged proteins are selectively eluted with imidazole-containing buffers.

Antibodies to NHP Products

Antibodies that specifically recognize one or more epitopes of a NHP, or epitopes of conserved variants of a NHP, or peptide fragments of a NHP are also encompassed by the invention. Such antibodies include but are not limited to polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above. Antibodies, and applications are uses thereof, similar to those contemplated herein are described in U.S. Pat. No. 5,474,901 the disclosure of which is herein incorporated by reference in its entirety.

The antibodies of the invention can be used, for example, in the detection of NHP in a biological sample and may, therefore, be utilized as part of a diagnostic or prognostic technique whereby patients may be tested for abnormal amounts of NHP. Such antibodies may also be utilized in conjunction with, for example, compound screening schemes, as described, below, in Section 5.5, for the evaluation of the effect of test compounds on expression and/or activity of a NHP coding sequence product. Additionally, such antibodies can be used in conjunction gene therapy to, for example, evaluate the normal and/or engineered NHP-expressing cells prior to their introduction into the patient. Such antibodies may additionally be used as a method for the inhibition of abnormal NHP activity. Thus, such antibodies may, therefore, be utilized as part of treatment methods.

For the production of antibodies, various host animals may be immunized by injection with the NHP, an NHP peptide (e.g., one corresponding the a functional domain of an NHP), truncated NHP polypeptides (NHP in which one or more domains have been deleted), functional equivalents of the NHP or mutated variant of the NHP. Such host animals may include but are not limited to pigs, rabbits, mice, goats, and rats, to name but a few. Various adjuvants may be used to increase the immunological response, depending on the host species, including but not limited to Freund's adjuvant (complete and incomplete), mineral salts such as aluminum hydroxide or aluminum phosphate, surface active substances such as lysolecithin, pluronic polyols, polyanions, peptides, oil emulsions, and potentially useful human adjuvants such as BCG (bacille Calmette-Guerin) and *Corynebacterium parvum*. Alternatively, the immune response could be enhanced by combination and or coupling with molecules such as keyhole limpet hemocyanin, tetanus toxoid, diptheria toxoid, ovalbumin, cholera toxin or fragments thereof. Polyclonal antibodies are heterogeneous populations of antibody molecules derived from the sera of the immunized animals.

Monoclonal antibodies, which are homogeneous populations of antibodies to a particular antigen, may be obtained by any technique which provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Such technologies are described in U.S. Pat. Nos. 6,075, 181 and 5,877,397 and their respective disclosures which are herein incorporated by reference in their entirety.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 334:544–546) can be adapted to produce single chain antibodies against NHP sequence products. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include, but are not limited to: the F(ab')₂ fragments which can be produced by pepsin digestion of the antibody molecule and the Fab fragments which can be generated by reducing the disulfide bridges of the F(ab')₂ fragments. Alternatively, Fab expression libraries may be constructed (Huse et al., 1989, Science, 246:1275–1281) to allow rapid and easy identification of monoclonal Fab fragments with the desired specificity.

Antibodies to a NHP can, in turn, be utilized to generate anti-idiotype antibodies that "mimic" a given NHP, using techniques well known to those skilled in the art. (See, e.g., Greenspan & Bona, 1993, FASEB J 7(5):437–444; and Nissinoff, 1991, J. Immunol. 147(8):2429–2438). For example antibodies which bind to a NHP domain and competitively inhibit the binding of NHP to its cognate receptor/ligand can be used to generate anti-idiotypes that "mimic" the NHP and, therefore, bind and activate or neutralize a receptor, cofactor, ligand, or binding partner. Such anti-idiotypic antibodies or Fab fragments of such anti-idiotypes can be used in therapeutic regimens involving a NHP mediated pathway.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description. Such modifications are intended to fall within the scope of the appended claims. All cited puiblications, patents, and patent applications are herein incorporated by reference in their entirety.

What is claimed is:

1. An isolated nucleic acid molecule comprising the nucleotide sequence described in SEQ ID NO: 9.

2. An isolated nucleic acid molecule comprising a sequence that:

(a) encodes the amino acid sequence shown in SEQ ID NO: 10; and (b) hybridizes under highly stringent conditions to the nucleotide sequence of SEQ ID NO: 9 or the complement thereof wherein highly stringent conditions comprise washing in 0.1×SSC/0.1% SDS at 68° C.

* * * * *

SEQUENCE LISTING

```
<160> NUMBER OF SEQ ID NOS: 13

<210> SEQ ID NO 1
<211> LENGTH: 141
<212> TYPE: DNA
<213> ORGANISM: homo sapiens

<400> SEQUENCE: 1
atgaagtgtc tcgggaagcg caggggccag gcagctgctt tcctgcctct ttgctggctc     60
tttttgaaga ttctgcaacc ggggcacagc cacctttata acaaccgcta tgctggtcca    120
cagggaaaga aacttttgaa a                                              141

<210> SEQ ID NO 2
<211> LENGTH: 47
<212> TYPE: PRT
<213> ORGANISM: homo sapiens

<400> SEQUENCE: 2

Met Lys Cys Leu Gly Lys Arg Arg Gly Gln Ala Ala Ala Phe Leu Pro
 1               5                  10                  15

Leu Cys Trp Leu Phe Leu Lys Ile Leu Gln Pro Gly His Ser His Leu
            20                  25                  30

Tyr Asn Asn Arg Tyr Ala Gly Pro Gln Gly Lys Lys Leu Leu Lys
        35                  40                  45

<210> SEQ ID NO 3
<211> LENGTH: 264
<212> TYPE: DNA
<213> ORGANISM: homo sapiens

<400> SEQUENCE: 3
atgaagtgtc tcgggaagcg caggggccag gcagctgctt tcctgcctct ttgctggctc     60
tttttgaaga ttctgcaacc ggggcacagc cacctttata acaaccgcta tgctggtgat    120
aaagtgataa gatttattcc caaaacagaa gaggaagcat atgcactgaa gaaaatatcc    180
tatcaactta aggttggttc ctgcactaca ggtggacctg tggcagccca gcagtatctc    240
ctatgtatca gagggaacag ttac                                           264

<210> SEQ ID NO 4
<211> LENGTH: 88
<212> TYPE: PRT
<213> ORGANISM: homo sapiens
```

-continued

<400> SEQUENCE: 4

Met Lys Cys Leu Gly Lys Arg Arg Gly Gln Ala Ala Phe Leu Pro
1               5                   10                  15

Leu Cys Trp Leu Phe Leu Lys Ile Leu Gln Pro Gly His Ser His Leu
            20                  25                  30

Tyr Asn Asn Arg Tyr Ala Gly Asp Lys Val Ile Arg Phe Ile Pro Lys
        35                  40                  45

Thr Glu Glu Ala Tyr Ala Leu Lys Lys Ile Ser Tyr Gln Leu Lys
    50                  55                  60

Val Gly Ser Cys Thr Thr Gly Gly Pro Val Ala Ala Gln Gln Tyr Leu
65                  70                  75                  80

Leu Cys Ile Arg Gly Asn Ser Tyr
                85

<210> SEQ ID NO 5
<211> LENGTH: 741
<212> TYPE: DNA
<213> ORGANISM: homo sapiens

<400> SEQUENCE: 5
atgaagtgtc tcgggaagcg caggggccag gcagctgctt tcctgcctct ttgctggctc      60
tttttgaaga ttctgcaacc ggggcacagc cacctttata caaccgcta tgctggtgat     120
aaagtgataa gatttattcc caaaacagaa gaggaagcat atgcactgaa gaaaatatcc    180
tatcaactta aggtggacct gtggcagccc agcagtatct cctatgtatc agagggaaca    240
gttactgatg tccatatccc ccaaaatggt tcccgagccc tgttagcctt cttacaggaa    300
gccaacatcc agtacaaggt cctcatagaa gatcttcaga aaacactgga agggaagc     360
agcttgcaca cccagagaaa ccgaagatcc ctctctggat ataattatga agtttatcac    420
tccttagaag aaattcaaaa ttggatgcat catctgaata aaactcactc aggcctcatt    480
cacatgttct ctattggaag atcatatgag ggaagatctc tttttatttt aaagctgggc    540
agacgatcac gactcaaaag agctgtttgg atagactgtg gtattcatgc aagagaatgg    600
attggtcctg cctttgtca gtggtttgta aagaagtcc tagaaaacac agctcacaaa     660
tgtcaagaat gtactaaatt tacaaaatat ctctgccact accaaaacca caaagtatg    720
cttaatcttg taagtattga g                                              741

<210> SEQ ID NO 6
<211> LENGTH: 247
<212> TYPE: PRT
<213> ORGANISM: homo sapiens

<400> SEQUENCE: 6

Met Lys Cys Leu Gly Lys Arg Arg Gly Gln Ala Ala Phe Leu Pro
1               5                   10                  15

Leu Cys Trp Leu Phe Leu Lys Ile Leu Gln Pro Gly His Ser His Leu
            20                  25                  30

Tyr Asn Asn Arg Tyr Ala Gly Asp Lys Val Ile Arg Phe Ile Pro Lys
        35                  40                  45

Thr Glu Glu Ala Tyr Ala Leu Lys Lys Ile Ser Tyr Gln Leu Lys
    50                  55                  60

Val Asp Leu Trp Gln Pro Ser Ser Ile Ser Tyr Val Ser Glu Gly Thr
65                  70                  75                  80

Val Thr Asp Val His Ile Pro Gln Asn Gly Ser Arg Ala Leu Leu Ala

-continued

```
                85                  90                  95
Phe Leu Gln Glu Ala Asn Ile Gln Tyr Lys Val Leu Ile Glu Asp Leu
                100                 105                 110
Gln Lys Thr Leu Glu Lys Gly Ser Ser Leu His Thr Gln Arg Asn Arg
            115                 120                 125
Arg Ser Leu Ser Gly Tyr Asn Tyr Glu Val Tyr His Ser Leu Glu Glu
        130                 135                 140
Ile Gln Asn Trp Met His His Leu Asn Lys Thr His Ser Gly Leu Ile
145                 150                 155                 160
His Met Phe Ser Ile Gly Arg Ser Tyr Glu Gly Arg Ser Leu Phe Ile
                165                 170                 175
Leu Lys Leu Gly Arg Arg Ser Arg Leu Lys Arg Ala Val Trp Ile Asp
                180                 185                 190
Cys Gly Ile His Ala Arg Glu Trp Ile Gly Pro Ala Phe Cys Gln Trp
            195                 200                 205
Phe Val Lys Glu Val Leu Glu Asn Thr Ala His Lys Cys Gln Glu Cys
        210                 215                 220
Thr Lys Phe Thr Lys Tyr Leu Cys His Tyr Gln Asn His Lys Ser Met
225                 230                 235                 240
Leu Asn Leu Val Ser Ile Glu
                245
```

<210> SEQ ID NO 7
<211> LENGTH: 276
<212> TYPE: DNA
<213> ORGANISM: homo sapiens

<400> SEQUENCE: 7

```
atgaagtgtc tcgggaagcg cagggggccag gcagctgctt tcctgcctct ttgctggctc    60
tttttgaaga ttctgcaacc ggggcacagc cacctttata caaccgcta tgctggtgat    120
aaagtgataa gatttattcc caaaacagaa gaggaagcat atgcactgaa gaaatatcc    180
tatcaactta aggtcctca tagaagatct tcagaaaaca ctggagaagg gaagcagctt    240
gcacacccag agaaaccgaa gatccctctc tggata                              276
```

<210> SEQ ID NO 8
<211> LENGTH: 92
<212> TYPE: PRT
<213> ORGANISM: homo sapiens

<400> SEQUENCE: 8

```
Met Lys Cys Leu Gly Lys Arg Arg Gly Gln Ala Ala Ala Phe Leu Pro
1               5                   10                  15
Leu Cys Trp Leu Phe Leu Lys Ile Leu Gln Pro Gly His Ser His Leu
            20                  25                  30
Tyr Asn Asn Arg Tyr Ala Gly Asp Lys Val Ile Arg Phe Ile Pro Lys
        35                  40                  45
Thr Glu Glu Ala Tyr Ala Leu Lys Lys Ile Ser Tyr Gln Leu Lys
    50                  55                  60
Gly Pro His Arg Arg Ser Ser Glu Asn Thr Gly Glu Gly Lys Gln Leu
65                  70                  75                  80
Ala His Pro Glu Lys Pro Lys Ile Pro Leu Trp Ile
                85                  90
```

<210> SEQ ID NO 9
<211> LENGTH: 1311

-continued

```
<212> TYPE: DNA
<213> ORGANISM: homo sapiens

<400> SEQUENCE: 9
atgaagtgtc tcgggaagcg caggggccag gcagctgctt tcctgcctct ttgctggctc      60
tttttgaaga ttctgcaacc ggggcacagc cacctttata caaccgcta tgctggtgat     120 aaagtgataa gatttattcc caaaacagaa gaggaagcat atgcactgaa gaaaatatcc     180
tatcaactta aggtggacct gtggcagccc agcagtatct cctatgtatc agagggaaca     240
gttactgatg tccatatccc ccaaaatggt tcccgagccc tgttagcctt cttacaggaa     300
gccaacatcc agtacaaggt cctcatagaa gatcttcaga aacactgga agggaagc       360 agcttgcaca cccagagaaa ccgaagatcc ctctctggat ataattatga agtttatcac     420
tccttagaag aaattcaaaa ttggatgcat catctgaata aaactcactc aggcctcatt     480
cacatgttct ctattggaag atcatatgag ggaagatctc tttttatttt aaagctgggc     540
agacgatcac gactcaaaag agctgtttgg atagactgtg gtattcatgc aagagaatgg     600
attggtcctg ccttttgtca gtggtttgta aagaagctc ttctaacata taagagtgac     660
ccagccatga gaaaaatgtt gaatcatcta tatttctata tcatgcctgt gtttaacgtc     720
gatggatacc attttagttg gaccaatgat cgatttttgga gaaaaacaag gtcaaggaac     780
tcaaggtttc gctgccgtgg agtggatgcc aatagaaact ggaaagtgaa gtggtgtgat     840
gaaggagctt ctatgcaccc ttgtgatgac acatactgtg gccctttttcc agaatctgag     900 ccggaagtga aggctgtagc taacttcctt cgaaaacaca gaaagcacat tagggcttat     960
ctctcctttc atgcatatgc tcagatgtta ctgtatccct attcttacaa atatgcaaca    1020
attcccaatt ttagatgtgt ggaatctgca gcttataaag ctgtgaatgc acttcagtca    1080
gtatacgggg tacgatacag atatggacca gcctccacaa cgttgtatgt gagctctggt    1140
agctcaatgg attgggccta caaaaatgga ataccttatg catttgcttt cgaactacgt    1200
gacactggat attttggatt tttactccca gagatgctca tcaaacccac ctgtacagaa    1260
actatgctgg ctgtgaaaaa tatcacaatg cacctgctaa agaaatgtcc c             1311

<210> SEQ ID NO 10
<211> LENGTH: 437
<212> TYPE: PRT
<213> ORGANISM: homo sapiens

<400> SEQUENCE: 10

Met Lys Cys Leu Gly Lys Arg Arg Gly Gln Ala Ala Ala Phe Leu Pro
  1               5                  10                  15

Leu Cys Trp Leu Phe Leu Lys Ile Leu Gln Pro Gly His Ser His Leu
                 20                  25                  30

Tyr Asn Asn Arg Tyr Ala Gly Asp Lys Val Ile Arg Phe Ile Pro Lys
             35                  40                  45

Thr Glu Glu Ala Tyr Ala Leu Lys Lys Ile Ser Tyr Gln Leu Lys
         50                  55                  60

Val Asp Leu Trp Gln Pro Ser Ser Ile Ser Tyr Val Ser Glu Gly Thr
 65                  70                  75                  80

Val Thr Asp Val His Ile Pro Gln Asn Gly Ser Arg Ala Leu Leu Ala
                 85                  90                  95

Phe Leu Gln Glu Ala Asn Ile Gln Tyr Lys Val Leu Ile Glu Asp Leu
                100                 105                 110

Gln Lys Thr Leu Glu Lys Gly Ser Ser Leu His Thr Gln Arg Asn Arg
```

```
                115                 120                 125
Arg Ser Leu Ser Gly Tyr Asn Tyr Glu Val Tyr His Ser Leu Glu Glu
        130                 135                 140

Ile Gln Asn Trp Met His His Leu Asn Lys Thr His Ser Gly Leu Ile
145                 150                 155                 160

His Met Phe Ser Ile Gly Arg Ser Tyr Glu Gly Arg Ser Leu Phe Ile
                165                 170                 175

Leu Lys Leu Gly Arg Arg Ser Arg Leu Lys Arg Ala Val Trp Ile Asp
            180                 185                 190

Cys Gly Ile His Ala Arg Glu Trp Ile Gly Pro Ala Phe Cys Gln Trp
        195                 200                 205

Phe Val Lys Glu Ala Leu Leu Thr Tyr Lys Ser Asp Pro Ala Met Arg
    210                 215                 220

Lys Met Leu Asn His Leu Tyr Phe Tyr Ile Met Pro Val Phe Asn Val
225                 230                 235                 240

Asp Gly Tyr His Phe Ser Trp Thr Asn Asp Arg Phe Trp Arg Lys Thr
                245                 250                 255

Arg Ser Arg Asn Ser Arg Phe Arg Cys Arg Gly Val Asp Ala Asn Arg
            260                 265                 270

Asn Trp Lys Val Lys Trp Cys Asp Glu Gly Ala Ser Met His Pro Cys
        275                 280                 285

Asp Asp Thr Tyr Cys Gly Pro Phe Pro Glu Ser Glu Pro Glu Val Lys
    290                 295                 300

Ala Val Ala Asn Phe Leu Arg Lys His Arg Lys His Ile Arg Ala Tyr
305                 310                 315                 320

Leu Ser Phe His Ala Tyr Ala Gln Met Leu Leu Tyr Pro Tyr Ser Tyr
                325                 330                 335

Lys Tyr Ala Thr Ile Pro Asn Phe Arg Cys Val Glu Ser Ala Ala Tyr
            340                 345                 350

Lys Ala Val Asn Ala Leu Gln Ser Val Tyr Gly Val Arg Tyr Arg Tyr
        355                 360                 365

Gly Pro Ala Ser Thr Thr Leu Tyr Val Ser Ser Gly Ser Ser Met Asp
    370                 375                 380

Trp Ala Tyr Lys Asn Gly Ile Pro Tyr Ala Phe Ala Phe Glu Leu Arg
385                 390                 395                 400

Asp Thr Gly Tyr Phe Gly Phe Leu Leu Pro Glu Met Leu Ile Lys Pro
                405                 410                 415

Thr Cys Thr Glu Thr Met Leu Ala Val Lys Asn Ile Thr Met His Leu
            420                 425                 430

Leu Lys Lys Cys Pro
            435

<210> SEQ ID NO 11
<211> LENGTH: 1050
<212> TYPE: DNA
<213> ORGANISM: homo sapiens

<400> SEQUENCE: 11
atgaagtgtc tcgggaagcg caggggccag gcagctgctt tcctgcctct ttgctggctc      60 ttttttgaaga ttctgcaacc ggggcacagc cacctttata caaccgcta tgctggtgat    120 aaagtgataa gatttattcc caaaacagaa gaggaagcat atgcactgaa gaaaatatcc    180
tatcaactta aggtggacct gtggcagccc agcagtatct cctatgtatc agagggaaca    240
gttactgatg tccatatccc ccaaaatggt tcccgagccc tgttagcctt cttacaggaa    300
```

-continued

```
gccaacatcc agtacaaggt cctcatagaa gatcttcaga aaacactgga gaagggaagc      360
agcttgcaca cccagagaaa ccgaagatcc ctctctggat ataattatga agtttatcac      420
tccttagaag aaattcaaaa ttggatgcat catctgaata aaactcactc aggcctcatt      480
cacatgttct ctattggaag atcatatgag ggaagatctc tttttatttt aaagctgggc      540
agacgatcac gactcaaaag agctgtttgg atagactgtg gtattcatgc aagagaatgg      600
attggtcctg ccttttgtca gtggtttgta aaagaagctc ttctaacata taagagtgac      660
ccagccatga gaaaaatgtt gaatcatcta tatttctata tcatgcctgt gtttaacgtc      720
gatggatacc attttagttg gaccaatgat cgattttgga gaaaaacaag gtcaaggaac      780
tcaaggtttc gctgccgtgg agtggatgcc aatagaaact ggaaagtgaa gtggtgtgat      840
gaaggagctt ctatgcaccc ttgtgatgac acatactgtg gcccttttcc agaatctgag      900
ccggaagtga aggctgtagc taacttcctt cgaaaacaca gaaagcacat tagggcttat      960
ctctcctttc atgcatatgc tcagatgtta ctgtatccct attcttacaa atatgcaaca     1020
attcccaatt ttagatgtgt ggtaagtatt                                      1050
```

<210> SEQ ID NO 12
<211> LENGTH: 350
<212> TYPE: PRT
<213> ORGANISM: homo sapiens

<400> SEQUENCE: 12

```
Met Lys Cys Leu Gly Lys Arg Arg Gly Gln Ala Ala Ala Phe Leu Pro
  1               5                  10                  15

Leu Cys Trp Leu Phe Leu Lys Ile Leu Gln Pro Gly His Ser His Leu
                 20                  25                  30

Tyr Asn Asn Arg Tyr Ala Gly Asp Lys Val Ile Arg Phe Ile Pro Lys
             35                  40                  45

Thr Glu Glu Ala Tyr Ala Leu Lys Lys Ile Ser Tyr Gln Leu Lys
         50                  55                  60

Val Asp Leu Trp Gln Pro Ser Ser Ile Ser Tyr Val Ser Glu Gly Thr
 65                  70                  75                  80

Val Thr Asp Val His Ile Pro Gln Asn Gly Ser Arg Ala Leu Leu Ala
                 85                  90                  95

Phe Leu Gln Glu Ala Asn Ile Gln Tyr Lys Val Leu Ile Glu Asp Leu
                100                 105                 110

Gln Lys Thr Leu Glu Lys Gly Ser Ser Leu His Thr Gln Arg Asn Arg
            115                 120                 125

Arg Ser Leu Ser Gly Tyr Asn Tyr Glu Val Tyr His Ser Leu Glu Glu
        130                 135                 140

Ile Gln Asn Trp Met His His Leu Asn Lys Thr His Ser Gly Leu Ile
145                 150                 155                 160

His Met Phe Ser Ile Gly Arg Ser Tyr Glu Gly Arg Ser Leu Phe Ile
                165                 170                 175

Leu Lys Leu Gly Arg Arg Ser Arg Leu Lys Arg Ala Val Trp Ile Asp
            180                 185                 190

Cys Gly Ile His Ala Arg Glu Trp Ile Gly Pro Ala Phe Cys Gln Trp
        195                 200                 205

Phe Val Lys Glu Ala Leu Leu Thr Tyr Lys Ser Asp Pro Ala Met Arg
    210                 215                 220

Lys Met Leu Asn His Leu Tyr Phe Tyr Ile Met Pro Val Phe Asn Val
225                 230                 235                 240
```

```
Asp Gly Tyr His Phe Ser Trp Thr Asn Asp Arg Phe Trp Arg Lys Thr
              245                 250                 255

Arg Ser Arg Asn Ser Arg Phe Arg Cys Arg Gly Val Asp Ala Asn Arg
          260                 265                 270

Asn Trp Lys Val Lys Trp Cys Asp Glu Gly Ala Ser Met His Pro Cys
      275                 280                 285

Asp Asp Thr Tyr Cys Gly Pro Phe Pro Glu Ser Glu Pro Glu Val Lys
  290                 295                 300

Ala Val Ala Asn Phe Leu Arg Lys His Arg Lys His Ile Arg Ala Tyr
305                 310                 315                 320

Leu Ser Phe His Ala Tyr Ala Gln Met Leu Leu Tyr Pro Tyr Ser Tyr
              325                 330                 335

Lys Tyr Ala Thr Ile Pro Asn Phe Arg Cys Val Val Ser Ile
          340                 345                 350

<210> SEQ ID NO 13
<211> LENGTH: 2128
<212> TYPE: DNA
<213> ORGANISM: homo sapiens

<400> SEQUENCE: 13
attaaagatc aggtcagctg ctgctgctgc tgctgctgct tgtcccaaga ccaagtcgta      60
atagcaactt cccttcctca gctgcctgaa ctttttttt cccttgtagc tggagagaag     120
tgtcacattt tgctcactct caaccttcct cgcccacccc cttcccggag aacctgtgcg     180
gtgtgtagag ggtgctgtga gccacctcca gcctcgggtg gctgcttaag taactttcaa     240
ctcctctctt cttaacacta tgaagtgtct cgggaagcgc aggggccagg cagctgcttt     300
cctgcctctt tgctggctct ttttgaagat tctgcaaccg gggcacagcc acctttataa     360
caaccgctat gctggtccac agggaaagaa acttttgaaa taataatcag ttgcctggta     420
tactgctcaa tgatattgcc acacgtaaga acaagcatac agtgataaag tgataagatt     480
tattcccaaa acagaagagg aagcatatgc actgaagaaa atatcctatc aacttaaggt     540
tggttcctgc actacaggtg gacctgtggc agcccagcag tatctcctat gtatcagagg     600
gaacagttac tgatgtccat atcccccaaa atggttcccg agccctgtta gccttcttac     660
aggaagccaa catccagtac aaggtcctca tagaagatct tcagaaaaca ctggagaagg     720
gaagcagctt gcacacccag agaaaccgaa gatccctctc tggatataat tatgaagttt     780
atcactcctt agaagaaatt caaaattgga tgcatcatct gaataaaact cactcaggcc     840
tcattcacat gttctctatt ggaagatcat atgagggaag atctcttttt attttaaagc     900
tgggcagacg atcacgactc aaaagagctg tttggataga ctgtggtatt catgcaagag     960
aatggattgg tcctgccttt tgtcagtggt ttgtaaaaga agtcctagaa aacacagctc    1020
acaaatgtca agaatgtact aaatttacaa aatatctctg ccactaccaa aaccacaaaa    1080
gtatgcttaa tcttgtaagt attgagtaat aaaatttct aaacattcct aaaaactctt    1140
ctaacatata agagtgaccc agccatgaga aaaatgttga atcatctata tttctatatc    1200
atgcctgtgt ttaacgtcga tggataccat tttagttgga ccaatgatcg atttttggaga    1260 aaacaaggt caaggaactc aaggtttcgc tgccgtggag tggatgccaa tagaaactgg    1320
aaagtgaagt ggtgtgatga aggagcttct atgcaccctt gtgatgacac atactgtggc    1380 cctttccag aatctgagcc ggaagtgaag gctgtagcta acttccttcg aaaacacaga    1440
aagcacatta gggcttatct ctcctttcat gcatatgctc agatgttact gtatccctat    1500
```

-continued

```
tcttacaaat atgcaacaat tcccaatttt agatgtgtgg aatctgcagc ttataaagct      1560
gtgaatgcac ttcagtcagt atacggggta cgatacagat atggaccagc ctccacaacg      1620
ttgtatgtga gctctggtag ctcaatggat tgggcctaca aaaatggaat accttatgca      1680
tttgctttcg aactacgtga cactggatat tttggatttt tactcccaga gatgctcatc      1740
aaacccacct gtacagaaac tatgctggct gtgaaaaata tcacaatgca cctgctaaag      1800
aaatgtccct gagacagccc aaggctcaag tcaactgcca taggattctg agcaaggcct      1860
acttggccct ggatagaaat tgttttcaaa gagaagggca gctgcttaga gtgaacatgt      1920
ctatggactt taaaaagacc ccacgcaatt ttgacttttt tgggggccaa tttggaaaaa      1980
acagttaagt atttgaccct gtgcatgtac atcaggcttc atgctgcttt tctgaagcta      2040
agatggttct aagtactaat gataatggca aacacatgtt tgtgtttatc ctaataaata      2100
ttttacatgt gaaaaaaaaa aaaaaaa                                         2128
```